US008741662B2

(12) United States Patent
Van Eyk et al.

(10) Patent No.: US 8,741,662 B2
(45) Date of Patent: Jun. 3, 2014

(54) ALBUMIN-BOUND PROTEIN/PEPTIDE COMPLEX AS A BIOMARKER FOR DISEASE

(75) Inventors: Jennifer E. Van Eyk, Baltimore, MD (US); Rebekah Lynn Gundry, Baltimore, MD (US); Robert J. Cotter, Baltimore, MD (US)

(73) Assignee: The Johns Hopkin University, Baltimore, MD (US)

( * ) Notice: Subject to any disclaimer, the term of this patent is extended or adjusted under 35 U.S.C. 154(b) by 1136 days.

(21) Appl. No.: 12/304,895

(22) PCT Filed: Jun. 14, 2007

(86) PCT No.: PCT/US2007/013968
§ 371 (c)(1),
(2), (4) Date: Oct. 16, 2009

(87) PCT Pub. No.: WO2007/146385
PCT Pub. Date: Dec. 21, 2007

(65) Prior Publication Data
US 2011/0143453 A1 Jun. 16, 2011

Related U.S. Application Data

(60) Provisional application No. 60/813,761, filed on Jun. 14, 2006, provisional application No. 60/813,825, filed on Jun. 15, 2006.

(51) Int. Cl.
*G01N 33/564* (2006.01)
*G01N 30/02* (2006.01)
*G01N 33/00* (2006.01)

(52) U.S. Cl.
USPC .............. 436/506; 435/2; 435/13; 435/287.1; 435/288.6; 436/518; 436/536; 436/541; 436/87; 436/88; 436/161; 436/171; 436/811; 530/362; 530/364

(58) Field of Classification Search
USPC ........... 435/7.1, 2, 13, 287.1, 288.6; 436/506, 436/87, 88, 811, 518, 536, 541, 161, 171; 530/362, 385, 364
See application file for complete search history.

(56) References Cited

U.S. PATENT DOCUMENTS

| 5,767,243 A | 6/1998 | Lichenstein et al. |
| 7,211,395 B2 * | 5/2007 | Sato et al .................... 435/7.1 |
| 2003/0069395 A1 | 4/2003 | Sato et al. |

FOREIGN PATENT DOCUMENTS

| WO | WO-2005/036180 A1 | 4/2005 |
| WO | WO 2005/117952 A2 | 12/2005 |
| WO | WO-2006/034427 A2 | 3/2006 |
| WO | WO 2005/117952 A3 | 4/2006 |

OTHER PUBLICATIONS

Cotter et al. Miniaturized mass spectrometers, the "albuminome" and biomarker discovery, Abstracts of Papers American Chemical Society: ABSTRACT, vol. 231 (Mar. 2006).*
Lopez et al. High Resolution Serum Proteomic Profiling of Alzheimer Disease Samples Reveals Disease-Specific , Carrier-Protein-Bound Mass Signatures, Clinical Chemistry 51 (10): 1946-1954 (2005).*

(Continued)

*Primary Examiner* — Gail R Gabel
(74) *Attorney, Agent, or Firm* — Venable LLP; Stefan J. Kirchanski

(57) ABSTRACT

Methods and kits for diagnosis and prognosis using biomarkers comprising albumin-bound protein/peptide complex (ABPPC).

7 Claims, 13 Drawing Sheets

(56) References Cited

OTHER PUBLICATIONS

Strongin. Sensitivity, Specificity, and Predictive Value of Diagnostic Tests: Definitions and Clinical Applications, Laboratory Diagnosis of Viral Infections, Lennette, E., ed., Marcel Dekker Inc., New York, pp. 211-219 (1993).*
International Search Report, dated Jul. 25, 2008, issued in connection with International Application No. PCT/US2007/013968.
Database MEDLINE, Accession No. 78042304, Smith, S.J., "Acute-phase proteins from the liver and enzymes from myocardial infarction; a qualitative relationship,"*Clinica Chimica Acta: International Journal of Clinical Chemistry*, Nov. 15, 1977, vol. 81, No. 1, pp. 75-85, see Abstract.
Database MRDLINE, Accession No. 80045470, Ballantyne D., "Response of plasma lipoproteins and acute phase proteins to myocardial infarction," *Clinica Chimica Acta: International Journal of Clinical Chemistry*, Nov. 15, 1979, vol. 99, No. 1, pp. 85-92, see Abstract.
Database MEDLINE, Accession No. 80135333, Andreasen, T., "Automated two0-stage assay for determination of antithrombin III with a centrifugal analyzer," *Haemostasis*, 1980, vol. 9, No. 2, pp. 65-70, see Abstract.
Written Opinion of the International Searching Authority in corresponding International Appln. No. PCT/US07/13968, dated Jul. 25, 2008.
Smith et al., Clinica Chimica Acta: International Journal of Clinical Chemistry, "Acute-phase proteins from the liver and enzymes from myocardial infarction; a qualitative relationship", Nov. 15, 1977, 81(1): pp. 75-85 (Abstract).
Ballantyne et al., Clinica Chimica Acta: International Journal of Clinical Chemistry, "Response of plasma lipoproteins and acute phase proteins to mycardial infarction", Nov. 15, 1979, 99(1): pp. 85-92 (Abstract).
Andreasen T., Haemostasis "Automated two-stage assay for retermination of antithrombin III with a crntrifugal analyser", (1980) 9(2): pp. 65-70 (Abstract).
Lind et al., Angiology, "Risk of mycocardial infarction in relation to plasma levels of homocysteine and inflamation-sensitive proteins: long-term nested case-control study", Jul./Aug. 2003, 54(4): pp. 401-410.
Extended European Search Report dated Jun. 18, 2010, issued in related European Patent Application No. 07809552.8.
Stanley et al., "Heart disease, clinical proteomics and mass spectometry," Disease Markers 20:167-178 (2004).
Lopez et al., "High-resolution serum proteomic profiling of alzheimer disease samples reveals disease-specific, carrier-protein-bound mass signatures," Clinical Chemistry, 51:10 p. 1946-1954 (2005).
Cotter et al., "Miniaturized mass spectrometers, the "albuminome" and biomarker discovery," Abstracts of Papers of American Chemical Society, 231st National Meeting of the American Chemical Society, Atlanta, GA, (2006). ANYL 14.
Yuen et al. "Ischemic and nephrotoxic acute renal failure are distinguished by their broad transcriptomic responses," Physical Genomics 25:375-386, (2006).
Gundry, R.L. et al., "Investigation of an albumin-enriched fraction of human serum and its albuminome," Proteomics Clin. Appl., (2007), vol. 1, No. 1, pp. 73-88.
Cotter, R.J. et al., "Tandem Time-of-Flight (TOF/TOF) Mass Spectrometry and Proteomics," J. Mass Spectrom. Soc. Japan, (2005), vol. 53, No. 1, pp. 7-17.

* cited by examiner

ALBUMIN-BOUND PROTEIN/PEPTIDE COMPLEX AS A BIOMARKER FOR DISEASE

This application is a Section 371 filing of PCT/US2007/013968, filed Jun. 14, 2007, and claims priority to U.S. provisional application Nos. 60/813,761, filed Jun. 14, 2006 and 60/813,825, filed Jun. 15, 2006, all of which are incorporated herein in their entirety.

This invention was made with funds under a contract with an agency of the United States Government, NIH N01-HV28-180. The U.S. government has certain rights in the invention.

FIELD OF INVENTION

The invention relates to methods of diagnosis using biomarkers comprising albumin-bound protein/peptide complex (ABPPC).

BACKGROUND

Serum albumin is the most abundant protein in serum, typically present at 45-50 mg/ml. Albumin functions as a "molecular sponge" binding proteins, lipids, and small molecules in the intracellular space (1-3) and has been found to form associations with peptide hormones, serum amyloid A, interferons, glucagons, bradykinin, insulin, and *Streptococcal* Protein G (4-7) but an extensive list of binding partners, and whether these partners change with disease, has not been investigated. Previous studies have shown a higher recovery of low molecular weight species when removing high molecular weight species under denaturing conditions, further confirming that larger proteins, such as albumin, are binding peptides (8). Furthermore, albumin has been reported to bind to a small number of specific proteins such as paraoxonase 1 (9), alpha-1-acid glycoprotein (10), and clusterin (11) (indirect interaction through paraoxonase 1) and apolipoprotein $E^{12}$ in serum. Although albumin binding peptides (below 30 kDa) in serum have been studied, the extent of their binding is currently unknown (13). To date, a comprehensive study of the whole proteins bound to albumin has not been carried out. Additionally, there is no documentation of any changes in the protein/peptide composition, ratio or PTM status of the proteins/peptides bound to albumin.

Albumin has been found to change with disease which alters its binding to metals and currently functions as a biomarker for ischemia. A modification of albumin that has previously been identified as a biomarker for myocardial ischemia is the N-terminus N-acetylation of albumin, which decreases the binding affinity of albumin to cobalt and nickel (21-23). Current patents (24,25) cover the usage of this N-terminal modification of albumin for ischemia and have led to a clinical assay for albumin cobalt binding (ACB assay). In addition to the N-terminal modification, the oxidation of albumin has been proposed to be a marker for oxidative stress (26). MALDI-TOF analysis (Matrix Assisted Laser Desorption/Ionization Time-of-Flight) of the albumin in patients with renal impairment and end-stage renal disease show an increase in the MW of albumin with disease (27). Finally, the fatty acid transport function of albumin is modified in atherosclerosis and diabetes (28). In patients with diabetes, the binding capacity of albumin for fatty acids is increased, and in patients with atherosclerosis the capacity is decreased. In conclusion, the evidence the albumin is changing with disease is clear. What has not been investigated or described previously is altered binding of proteins and/or peptides to albumin in serum. The current work is unique because it includes the analysis of intact proteins, degraded proteins, and peptides, without eliminating any mass range. Furthermore, the current work focuses on the changes in the proteins and peptides that bind to albumin, a feature not addressed in any previous literature.

SUMMARY

We examined an albumin-enriched fraction of human serum in order to determine any albumin binding proteins in healthy individuals and furthermore whether the proteins that bind to albumin change with disease. The study included multiple independent methods for isolation of albumin and any bound proteins/peptides (modified and nonmodified) (albumin bound protein/peptide complex, ABPPC) (FIG. 1). The results show that ABPPC should be useful biomarkers for disease.

Accordingly, a method of diagnosing a disease or disorder is provided, comprising measuring the level of specific albumin-bound protein/peptide complex(es) (ABPPC) in a subject, and comparing the level to a control level from a normal subject population. It has been found that variations in the levels of specific ABPPCs, and variations in ABPPC profile are indicative of specific diseases and disorders.

The aim is to characterize proteins that are differentially bound to albumin in diseased and healthy patients in a cost effective, rapid and sensitive manner that is compatible with current blood collection protocols. This is based on the hypothesis that albumin changes with disease, and therefore the complex of albumin with its bound proteins and peptides changes, although the inventors are not bound by any particular hypothesis. The ABPPC assay may measure a modification of albumin or a change in ABPPC composition (i.e. the presence or absence of one or more proteins, altered concentration (or stoichiomery or molar ratio) of one or more proteins, change in a protein's PTM (e.g. proteolysis fragment vs. intact protein including albumin).

The method can be used alone, or in conjunction with other diagnostic tests to improve the accuracy and specificity of the diagnosis. It can also be used for screening purposes, to identify individuals who appear to be "at risk" for further testing by this or other means.

Accordingly, in one aspect, the method comprises (a) measuring the level of at least one biomarker in a biological sample obtained from said subject, wherein said biomarker comprises an albumin-bound protein/peptide complex (ABPPC), and (b) comparing the level measured in the biological sample to a control level in a normal subject population, wherein an increase or decrease in the level, compared to control level, is indicative of said disease or disorder.

In another aspect, the method comprises assaying a subject sample for the presence of at least one biomarker comprising an albumin-bound protein/peptide complex (ABPPC); wherein the detection of said biomarker(s) is correlated with a diagnosis of the disease or disorder, the correlation taking into account the presence and level of biomarker(s) in the subject sample as compared to normal subjects.

The biomarkers can be detected by any suitable means known to those of skill in the art, for example, using a protein assay, binding assay, or an immunoassay. Biomarkers may also be identified as peaks using Mass Spectroscopy, or as gel bands using, for example size exclusion chromatography (SEC), optionally after appropriate initial treatment of the sample. Exemplary assays are described in detail in the examples which follow. For a positive diagnosis, the biomarkers are elevated or lowered as compared to values in normal healthy controls.

The subject sample may be selected, for example, from the group consisting of blood, blood plasma, serum. Preferably, the sample is albumin-enriched serum.

The diagnostic assay can be used, for example, to evaluate patients presenting to an emergency room, or for ongoing care within a hospital setting, or in a medical practitioner's office. The assay has the advantage that it can be easily and reproducibly obtained from individuals since albumin is highly abundant in serum (40-50 mg/ml). Specific antibodies to albumin are available and the ABPPC can be captured easily without a complicated assay. Other biochemical methods can be used as well, including liquid chromatography and gel based methods. Since the capture of ABPPC is based upon targeting albumin, the proteins (or a PTM or other modification) that are changing in a particular disease need not be known in advance, since the protocol for capturing the ABPPC is universal for all diseases. In this way, the ABPPC is a simple targeted assay that casts a wide net over a variety of potential targets and is, therefore, very cost effective. There is no requirement for developing multiple specific antibodies to detect low abundance proteins, for example. Furthermore, capturing this naturally-occurring sub-proteome reduces sample complexity and avoids the problems associated with assay sensitivity at low protein concentrations. Since some proteins in the ABPPC have not been observed in albumin depleted serum, it appears that some biomarkers are unique to the ABPPC.

After a protein of interest has been identified, downstream clinical assays could simply couple one capture antibody for albumin to a different detecting antibody for the protein of interest.

Also provided is a kit for carrying out the method described herein. In one embodiment, the kit may comprise, for example, any of: an antibody (or a chemical moiety) to specifically capture or enrich for the endogenous albumin), a secondary antibody (or chemical moiety) to one or more of the specific protein (or peptide or modified protein) bound to albumin and components for detection and/or quantification of the amount of secondary antibody bound. In one embodiment, the secondary antibody would be against protein(s) that change with the specific protein so that one is quantifying the change in protein content of the ABPPC.

An alternative would be a capture of endogenous ABPPC (with an antibody or chemical moiety) with a direct detection of the protein(s) of interest using mass spectrometry of the intact or enzymatically degraded protein. In this embodiment the kit may contain the anti-albumin antibody coupled to a matrix (for example, in a small column or packed into an end of a pipette tip) where the ABPPC would be enriched followed elution into MS for intact mass or eluted for digestion and subsequent MS analysis (of all peptides or specific signature peptide for the analyte(s)). Kits of the invention may contain a plurality of antibodies so that more than one ABPPC component could be assessed simultaneously.

It is also believed that the ratio of bound to free (circulating) ABPPC may be important. Methods and kits may be modified so that specific proteins are measured as bound to serum albumin or free. For example, in the current work, a number of proteins have been observed to be both bound to albumin, but also observed in the albumin-depleted fraction of serum, indicating that they could be present in their free form. Examples of these proteins include antithrombin III, apolipoprotein AII, AIV, CII, clusterin, transthyretin, and vitamin D binding protein, for example. Practitioners will be able to determine through routine experimentation how the ratio is altered in particular disease states.

It is a further object to provide a method of identifying biomarkers comprising ABPPC for specific diseases and disorders by screening populations of patients having a disease or disorder for serum ABPPCs and comparing the ABPPCs thus obtained with those in a normal subject population. Such screening can be carried out in the same manner as is done for the diagnostic assays described hereinabove. For example, methods such as Mass Spectroscopy or SEC can be used to determine a profile of ABPPCs and where differences are found, specific ABPPCs identified, e.g. using a protein assay, binding assay, or immunoassay, that will be useful as biomarkers. Furthermore, a protein digestion could be carried out and one or more of the resulting peptides monitored. Biomarkers so identified can be used in the diagnostic method described herein.

Diseases or disorders for which the methods and compositions of the invention are expected to be useful include vasculitis, myocardial infarction, heart failure, sepsis, cancer, and diabetes. Using the methods detailed herein, persons of skill in the art will be able to determine other diseases and disorders in which ABPPC is altered without undue experimentation This application claims priority to U.S. provisional applications No. 60/813,761, filed Jun. 14, 2007, and 60/813,825, filed Jun. 15, 2007, which are hereby incorporated by reference. References and patents cited herein are hereby incorporated by reference.

DETAILED DESCRIPTION

Definitions

Figure 1:
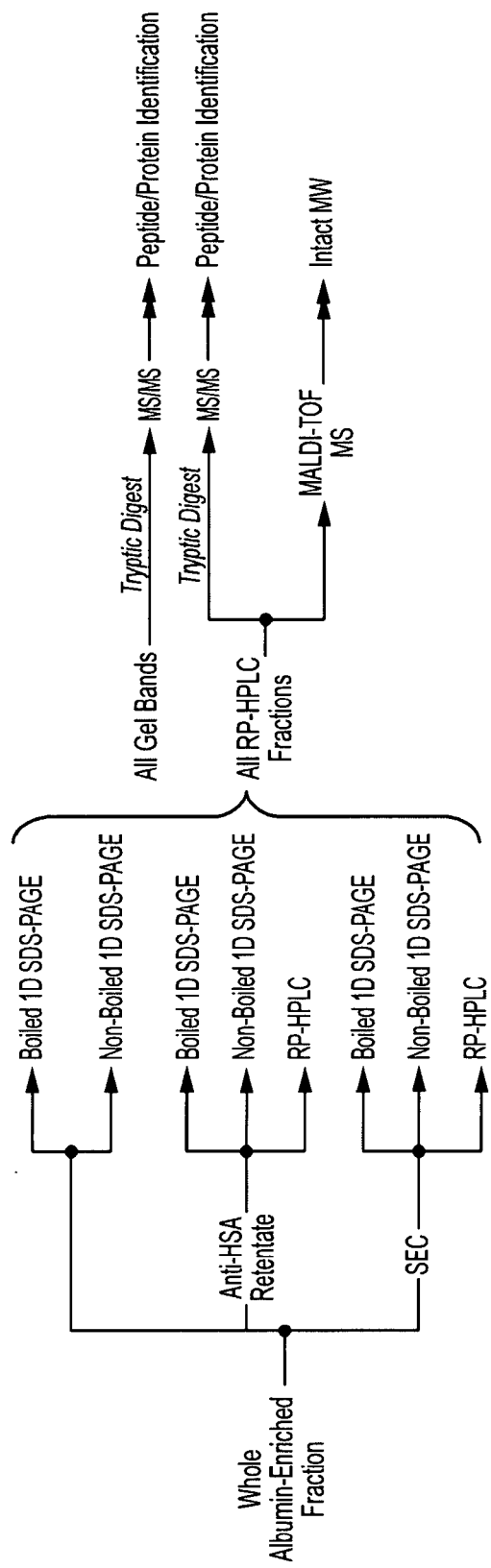
FIG. 1. Methods and corresponding objectives used to separate an albumin-enriched fraction and characterize the ABPPC.

The following terms are used as defined below throughout this application, unless otherwise indicated.

"Marker" or "biomarker" are used interchangeably herein, and in the context of the present invention refer to an ABPPC (of a particular specific identity or apparent molecular weight) which is differentially present in a sample taken from patients having a specific disease or disorder as compared to a control value, the control value consisting of, for example, average or mean values in comparable samples taken from control subjects (e.g., a person with a negative diagnosis, normal or healthy subject). Biomarkers may be identified as specific peptides or proteins, either presently bound or cleaved from albumin, or as specific peaks, bands, fractions, etc. in a mass spectroscopy, SEC, or other separation process or antibody detection. In some applications, for example, a mass spectroscopy or other profile or multiple antibodies may be used to identify multiple biomarkers, and differences between individual biomarkers and/or the partial or complete profile may be used for diagnosis.

The phrase "differentially present" refers to differences in the quantity and/or the frequency of a marker present in a sample taken from patients having a specific disease or disorder as compared to a control subject. For example, a marker can be a ABPPC which is present at an elevated level or at a decreased level in samples of patients with the disease or disorder compared to a control value (e.g. determined from samples of control subjects). Alternatively, a marker can be an ABPPC which is detected at a higher frequency or at a lower frequency in samples of patients compared to samples of control subjects. A marker can be differentially present in terms of quantity, frequency or both. It may also be a physical change/modification of the protein that is the marker, rather than just an increase or decrease in the amount present/detected. For example, it may be the post-translational modification, cleavage, or isoform of the protein that is changing, and it is this change that is detected by the assay. This is separate from measuring a different quantity in diseased vs. control.

A marker, compound, composition or substance is differentially present in a sample if the amount of the marker, compound, composition or substance in the sample is statistically significantly different from the amount of the marker, compound, composition or substance in another sample, or from a control value. For example, a compound is differentially present if it is present at least about 120%, at least about 130%, at least about 150%, at least about 180%, at least about 200%, at least about 300%, at least about 500%, at least about 700%, at least about 900%, or at least about 1000% greater or less than it is present in the other sample (e.g. control), or if it is detectable in one sample and not detectable in the other.

Alternatively or additionally, a marker, compound, composition or substance is differentially present between samples if the frequency of detecting the marker, etc. in samples of patients suffering from a particular disease or disorder, is statistically significantly higher or lower than in the control samples or control values obtained from healthy individuals. For example, a biomarker is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples. These exemplary values notwithstanding, it is expected that a skilled practitioner can determine cut-off points, etc. that represent a statistically significant difference to determine whether the marker is differentially present "Diagnostic" means identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g. when positive assay results are obtained). In the latter context, "detecting" and "diagnosing" are considered synonymous.

By "at risk of" is intended to mean at increased risk of, compared to a normal subject, or compared to a control group, e.g. a patient population. Thus a subject carrying a particular marker may have an increased risk for a specific disease or disorder, and be identified as needing further testing. "Increased risk" or "elevated risk" mean any statistically significant increase in the probability, e.g., that the subject has the disorder. The risk is preferably increased by at least 10%, more preferably at least 20%, and even more preferably at least 50% over the control group with which the comparison is being made.

A "test amount" of a marker refers to an amount of a marker present in a sample being tested. A test amount can be either in absolute amount (e.g., μg/ml) or a relative amount (e.g., relative intensity of signals).

A "diagnostic amount" of a marker refers to an amount of a marker in a subject's sample that is consistent with a diagnosis of a particular disease or disorder. A diagnostic amount can be either in absolute amount (e.g., μg/ml) or a relative amount (e.g., relative intensity of signals).

A "control amount" of a marker can be any amount or a range of amount which is to be compared against a test amount of a marker. For example, a control amount of a marker can be the amount of a marker in a person who does not suffer from the disease or disorder sought to be diagnosed. A control amount can be either in absolute amount (e.g., μg/ml) or a relative amount (e.g., relative intensity of signals).

The terms "polypeptide," "peptide" and "protein" are used interchangeably herein to refer to a polymer of α-amino acid residues, in particular, of naturally-occurring α-amino acids. The terms apply to amino acid polymers in which one or more amino acid residue is an analog or mimetic of a corresponding naturally-occurring amino acid, as well as to naturally-occurring amino acid polymers. Polypeptides can be modified, e.g., by the addition of carbohydrate residues to form glycoproteins, phosphorylation to form phosphoproteins, and a large number of chemical modifications (oxidation, deamidation, amidation, methylation, formylation, hydroxymethylation, guanidination, for example) as well as degraded, reduced, or crosslinked. The terms "polypeptide," "peptide" and, "protein" include all unmodified and modified forms of the protein "Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, flow cytometry, or direct anlaysis by mass spectreometry of intact or subsequentally digested peptides (one or more peptide can be assessed.)

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

By "binding assay" is meant a biochemical assay wherein the biomarkers are detected by binding to an agent, such as an antibody, through which the detection process is carried out. The detection process may involve radioactive or fluorescent labels, and the like. The assay may involve immobilization of the biomarker, or may take place in solution.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

The terms "subject", "patient" or "individual" generally refer to a human, although the methods of the invention are not limited to humans, and should be useful in other animals (e.g. birds, reptiles, amphibians, mammals), particularly in mammals, since albumin is homologous among species.

"Sample" is used herein in its broadest sense. A sample may comprise a bodily fluid including blood, serum, plasma, tears, aqueous and vitreous humor, spinal fluid; a soluble fraction of a cell or tissue preparation, or media in which cells were grown; a, aorganelle, or membrane isolated or extracted from a cell or tissue; polypeptides, or peptides in solution or bound to a substrate; a cell; a tissue; a tissue print; a fingerprint, skin or hair; fragments and derivatives thereof. Subject samples usually comprise derivatives of blood products, including blood, plasma and serum.

By "albumin-enriched serum or plasma" is meant serum or plasma that has been treated to reduce or remove components other than albumin and associated peptides and proteins which are bound thereto.

EXAMPLES

There are two primary methods available for isolating albumin from serum or plasma: affinity-based (e.g., antibody, cibacron blue) and chemical-based methods (e.g., NaCl/EtOH [30,31] TCA/acetone [32]). Many of the affinity-based methods have been compared and shown to effectively remove albumin [29, 33, 34]. However, these methods are vulnerable to non-specific binding of proteins/peptides to the ligand and column materials and carryover between experiments in the case of LC columns [29, 31, 33-36]. Alternatively, albumin has been purified using NaCl/EtOH since the 1940s [37] and this method is routinely used for isolating pharmaceutical grade albumin. Recently, this process was optimized for the proteomics field to minimize the steps required for effective purification and removal of albumin [30], but copurification of other proteins may still be an issue.

Example 1

Isolation of Albumin Enriched Fraction of Human Serum

Albumin depletion by chemical extraction was performed as described by Fu et al. [30]. Briefly, 100 µL normal human serum was depleted of lipids via centrifugation, followed by depletion of IgG using a protein G affinity column (Amersham Biosciences, Piscataway, N.J., USA). IgG depleted serum was brought to 42% ethanol/100 mM NaCl and incubated at 4° C. for 1 h followed by centrifugation at 16 000×g for 45 min. The supernatant (albumin-enriched fraction) was collected and used for the work presented below.

Example 2

Isolation and Characterization of ABPPC

Treatment of whole albumin-enriched fraction is shown schematically in FIG. 1. The study included multiple independent methods for isolation of albumin and any bound proteins/peptides (modified and unmodified)(albumin bound protein/peptide complex, ABPPC).

Figure 2:
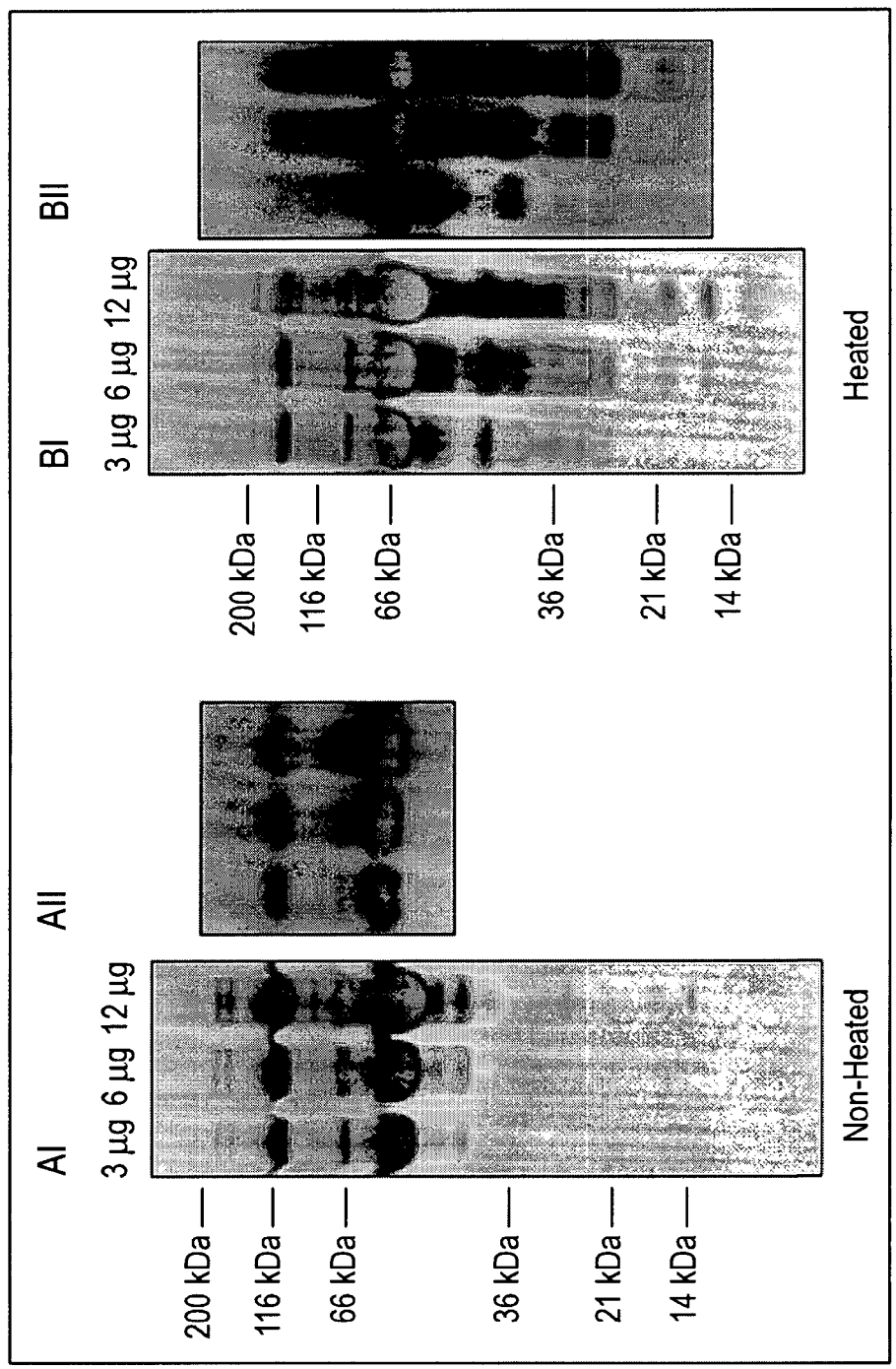
FIG. 2. 1D SDS-PAGE (AI, BI) and corresponding western blot for albumin (AII, BII) of the albumin-enriched fraction of normal pooled serum.

Initial analyses included 1D SDS-PAGE of heated and non-heated samples and a western blot for albumin (FIG. 2). On 1D SDS-PAGE, the disappearance of the 116 kDa band, which contains albumin, and the appearance of several bands only after severe denaturation (i.e. heating and treatment with 8M urea) indicate that many of the proteins/peptides in the albumin-enriched fraction were associated with albumin or other protein (FIG. 2 AI, BD. Importantly, these results were seen only when the gel was overloaded (6-12 µg/lane). The presence of the lower molecular weight bands were not visualized in lower loads of non-heated sample. By western blot, albumin is present in the 116 kDa band in the non-heated sample, running higher than its expected MW of 66 kDa (FIG. 2AII). However, upon heating, this band disappears and smaller MW bands, some containing albumin, appear (FIG. 2 BII). Therefore, it is possible that albumin is appearing at a higher molecular weight because it is forming a dimer or it is bound to one or more other proteins/peptides, and only upon severely denaturing conditions these proteins/peptides are released. Consistent with this is the fact that peptides from proteins other than albumin were identified in this 116 kDa band, including ceruloplasmin, haptoglobin, and alpha-1B-glycoprotein. It is noted that albumin runs at a lower molecular weight in the non-heated condition. This could be due to incomplete reduction of disulfides such that albumin is not fully saturated with SDS, which affects the migration, or that another protein or peptide bound to albumin is altering the migration of albumin in the gel. Furthermore, the presence of multiple albumin fragments after heating (FIG. 2BII) indicates that extensive proteolysis of albumin has occurred. In conclusion, while the 1D SDS-PAGE results are not conclusive evidence of proteins binding to albumin, these preliminary results prompted more sophisticated analyses by SEC and immunoaffinity chromatography.

Native size-exclusion chromatography (SEC) was used to separate the albumin-enriched fraction by size to isolate any protein complexes present in native conditions. SEC was chosen because it has minimal non-specific binding coupled with the ability to sort protein complexes by size under native conditions. Immunoaffinity by an anti-HSA spin column was chosen for its specificity for human albumin, though non-specific binding by, the matrix was an acknowledged drawback. An anti-albumin antibody affinity column (anti-HSA) was used to bind albumin and any bound proteins/peptides. The proteins bound to the column were then eluted from the column (anti-HSA retentate) prior to further analyses. The anti-HSA retentate and high MW SEC fractions were separated by 1D SDS-PAGE and reversed phase high performance liquid chromatography (RP-HPLC) in order to further separate the bound proteins/peptides from albumin prior to tryptic digestion and tandem mass spectrometry (MS/MS) for protein/peptide identification.

Figure 3:
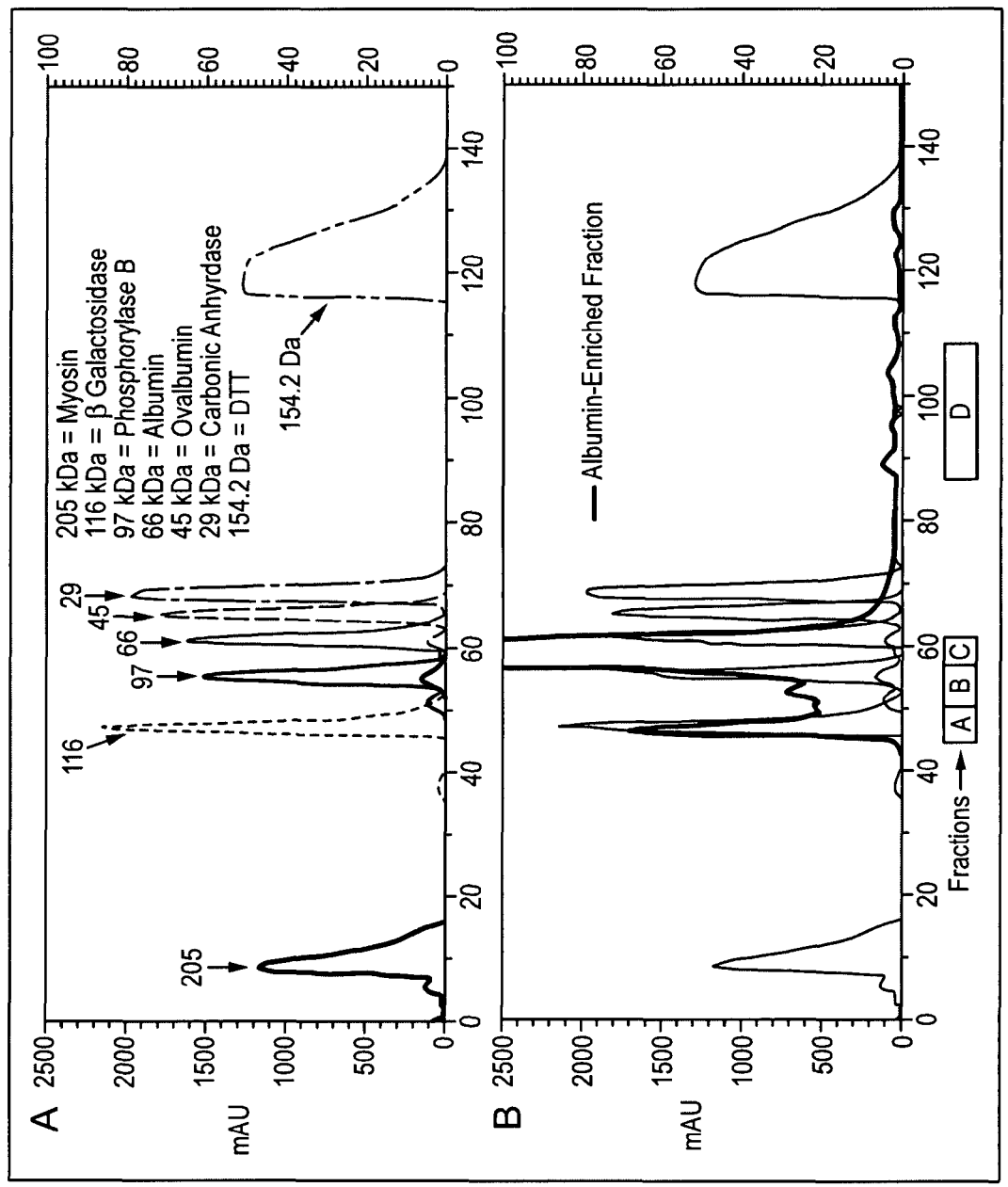
FIG. 3. SEC chromatograms. (A) MW standards (A) Albumin-enriched fraction overlaid on the MW standards.
Figure 4:
FIG. 4. SEC chromatograms (280 nm) of 8 consecutive injections of the albumin-enriched fraction from healthy individuals.

Native SEC was used to separate the albumin-enriched fraction by size, as larger proteins will spend less time on the column and elute earlier than smaller proteins and peptides. Under native conditions, it is expected that those proteins and peptides bound to albumin will elute in the fraction/s containing albumin, while those unbound will elute separately from albumin, consistent with their native molecular weights. SEC was successful in separating a wide range of proteins (29-205 kDa) with good resolution, as illustrated by well-separated peaks in FIG. 3A. The albumin-enriched fraction separated into 4 regions (A-D) by SEC, with the major peak eluting at the time consistent with a mass slightly larger than the 66 kDa standard protein (FIG. 3B). A benefit of SEC is that it is highly reproducible, as can be seen in FIG. 4.

Figure 5:
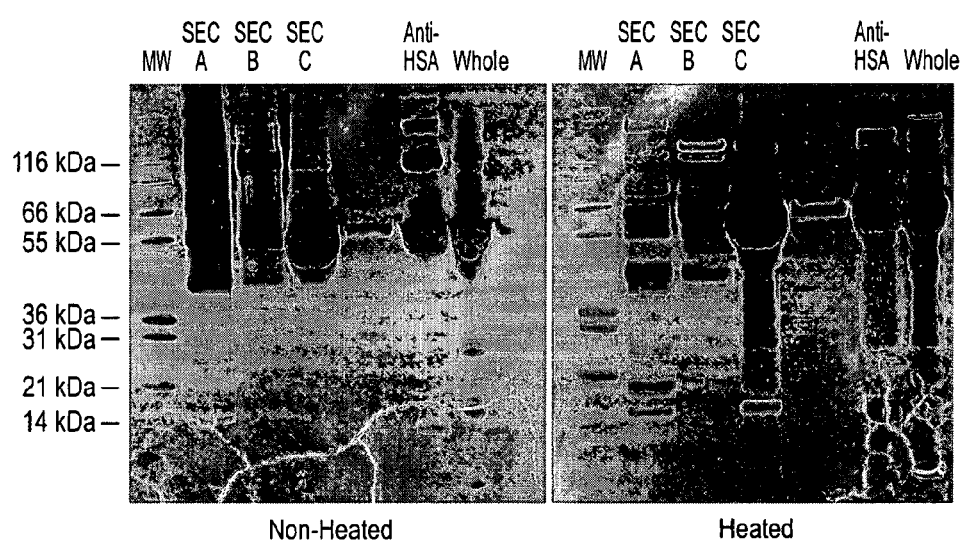
FIG. 5. 1D SDS-PAGE of heated and non-heated SEC fractions, anti-HSA (human serum albumin) retentate and the whole albumin-enriched fraction from normal pooled serum.
Figure 6:
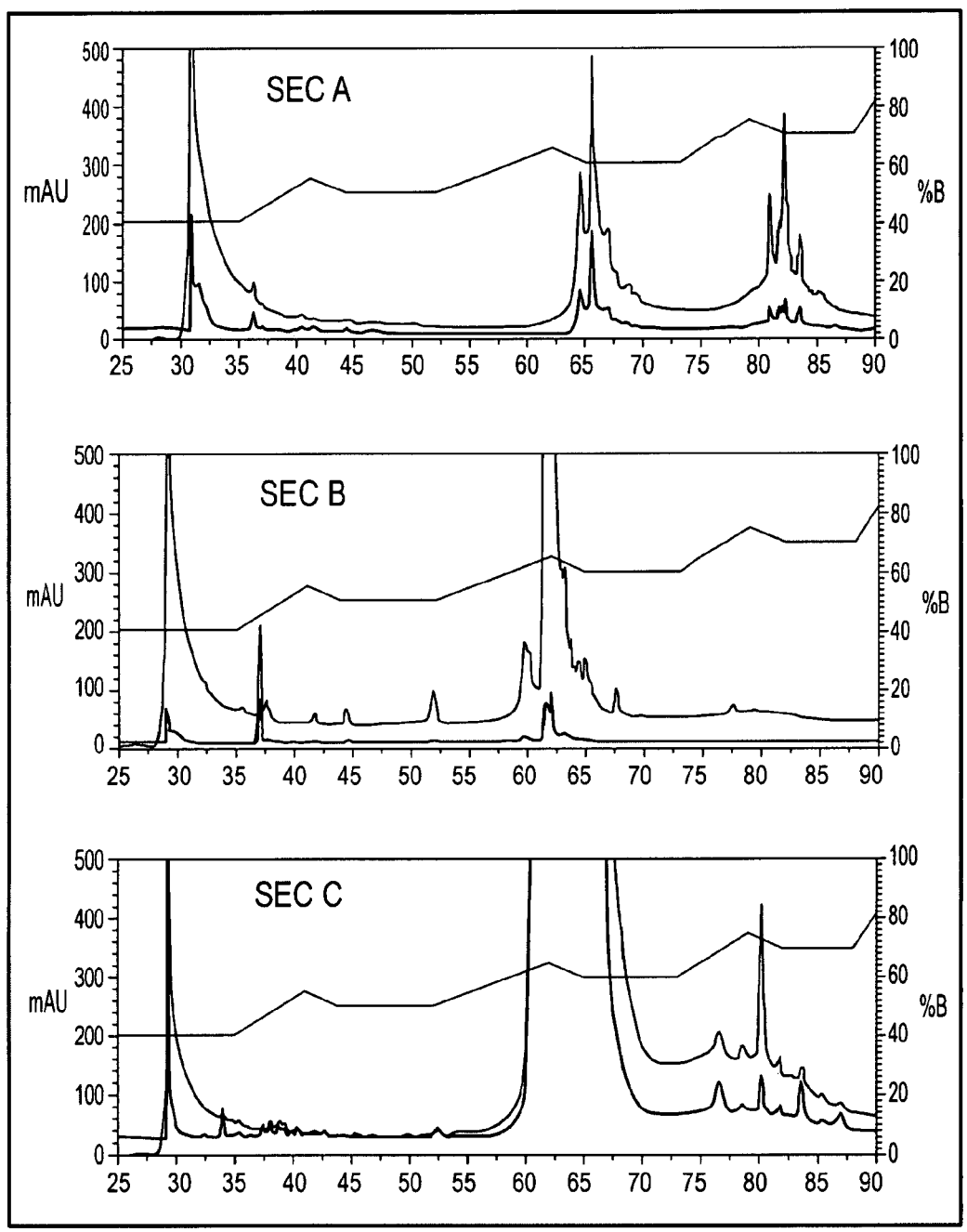
FIG. 6. RP-HPLC of three fractions (A-C) of the SEC chromatogram of the albumin-enriched fraction from normal pooled serum.

SEC-A contains fractions eluting near 116 kDa, SEC-B contains fractions from the tail of SEC-A and slope of SEC-C, SEC-C contains fractions eluting slightly above 66 kDa, and SEC-D contains sample from the lower molecular weight region. Each fraction (A-D) was then further separated and desalted prior to analysis by mass spectrometry. The SEC fractions were separated by two methods, 1D SDS-PAGE (FIG. 5) and RP-HPLC (FIG. 6) prior to MALDI-TOF MS and LC-MS/MS.

Example 3

Proteins Identified in the ABPPC

Analysis by 1D SDS-PAGE and RP-HPLC of the SEC fractions reveals the presence of multiple species in addition to albumin eluting in fractions A, B, and C. Interestingly, many of these proteins in the high MW SEC fractions have MW well below 66 kDa and the proteins are listed in Table 1.

TABLE 1

Proteins identified in the albumin-binding protein/peptide complex (ABPPC).

| | Protein | Intact? | Whole | SEC A | SEC B | SEC C | Anti-HSA Retentate | Bound? **, ***, # | In Depleted Serum? | Biomarker Class; Justification | Reference |
|---|---|---|---|---|---|---|---|---|---|---|---|
| 1 | Afamin | | ✓ | | ✓ | ✓ | ✓ | YES | ✓ | | |
| 2 | Alpha-1-acid glycoprotein 1 | YES | ✓ | ✓ | ✓ | ✓ | ✓ | YES | ✓ | Cardiovascular; Acute phase reactant | Anderson, 2005 |
| 3 | Alpha-1-acid glycoprotein | | ✓ | ✓ | | | ✓ | YES | ✓ | Cardiovascular; Assoc. w/ cardiovascular disease/diabetes | Berhane, 2005 |
| 4 | Alpha-1-antichymotrypsin | YES | ✓ | ✓ | ✓ | | ✓ | YES | ✓ | Cardiovascular; Inhibitor, plasma protease | Anderson, 2005 |
| 5 | Alpha-1-antitrypsin | YES | ✓ | ✓ | ✓ | | ✓ | YES | ✓ | Cardiovascular; Inhibitor, plasma protease | Anderson, 2005 |
| 6 | Alpha-1B-glycoprotein | YES | ✓ | ✓ | ✓ | ✓ | ✓ | YES | ✓ | Cardiovascular; Assoc. w/ arterial thrombotic disease | Gonzalez, 1996 |
| 7 | Alpha-2HS-glycoprotein | YES | ✓ | ✓ | ✓ | ✓ | ✓ | YES | | Cardiovascular; Changes assoc. w/acute myocardial infraction | Berhane, 2005 |
| 8 | Angiotensinogen | | ✓ | ✓ | | | ✓ | YES | ✓ | Cardiovascular; Precursor, blood pressure control | Anderson, 2005 |

TABLE 1-continued

Proteins identified in the albumin-binding protein/peptide complex (ABPPC).

| Protein | Intact? | Whole | SEC A | SEC B | SEC C | Anti-HSA Retentate | Bound? **, ***, # | In Depleted Serum? | Biomarker Class; Justification | Reference |
|---|---|---|---|---|---|---|---|---|---|---|
| 9 Antithrombin III | YES ** | ✓ | ✓ | | ✓ | ✓ | YES | ✓ | Cardiovascular; inhibitor, thrombin | Anderson, 2005 |
| 10 Apolipoprotein A I | YES | ✓ | ✓ | | ✓ | ✓ | YES | | Cardiovascular; Myocardial Infraction association | Anderson, 2005 |
| 11 Apolipoprotein A II | YES | ✓ | ✓ | | | ✓ | YES | ✓ | Cardiovascular; Lipoprotein | Anderson, 2005 |
| 12 Apolipoprotein A IV | YES | ✓ | ✓ | | ✓ | ✓ | YES | ✓ | Cardiovascular; Risk Factor, CHD | Anderson, 2005 |
| 13 Apolipoprotein C II | YES | ✓ | ✓ | | | ✓ | YES | ✓ | Cardiovascular; Lipoprotein | Anderson, 2005 |
| 14 Apolipoprotein C III | YES | ✓ | ✓ | | | ✓ | YES | | Cardiovascular; CHD Marker | Anderson, 2005 |
| 15 Carboxypeptidase B2 | | ✓ | | | ✓ | ✓ | YES | | Vascular and/or Coagulation Protein; Degrades vasodilator bradykinin | Berhane, 2005 |
| 16 Ceruloplasmin | YES ** | ✓ | | ✓ | ✓ | ✓ | YES | | Cardiovascular; Risk factor, cardiovascular disease | Anderson, 2005 |
| 17 Clusterin | YES | ✓ | ✓ | ✓ | | ✓ | YES | ✓ | Cardiovascular; Vascular Injury | Anderson, 2005 |
| 18 Complement component 1 inhibitor | YES | ✓ | | ✓ | | ✓ | YES | | Cardiovascular; Preserves ischemic myocardium from reprofusion injury | Anderson, 2005 |
| 19 Complement component 4A | | ✓ | ✓ | | | ✓ | YES | ✓ | Previous myocardial infraction assc. | Anderson, 2005 |
| 20 Haptoglobin | YES | ✓ | ✓ | ✓ | ✓ | ✓ | YES | ✓ | Cardiovascular; Assc. w/ higher serum total and free cholesterol | Anderson, 2005 |
| 21 Hemoglobin, alpha | YES | ✓ | ✓ | ✓ | | | YES | | Cardiovascular; Compensatory role, ischemic heart disease | Berhane, 2005 |
| 22 Hemoglobin, beta | YES | ✓ | ✓ | ✓ | ✓ | ✓ | YES | ✓ | | |
| 23 Hemopexin | YES | ✓ | ✓ | ✓ | ✓ | ✓ | YES | ✓ | Cardiovascular; Acute phase protein | Anderson, 2005 |
| 24 Hornerin | | | | | ✓ | ✓ | YES | | | |
| 25 Inter alpha trypsin inhibitor heavy chain H4 | | ✓ | ✓ | ✓ | | ✓ | YES | | Cardiovascular; Assoc. w/ hypercholesterolemia | Fujita, 2004 |
| 26 Kininogen | | ✓ | ✓ | ✓ | | ✓ | YES | | Cardiovascular; Cardiac protective profiles | Berhane, 2005 |
| 27 Leucine rich alpha 2 glycoprotein | YES | ✓ | ✓ | | | ✓ | YES | ✓ | | |
| 28 Paraoxonase 1 | | ✓ | ✓ | | ✓ | ✓ | YES | ✓ | Cardiovascular; Relation to cardiovascular disease | Anderson, 2005 |
| 29 Peptidoglycan recognition protein 2 | | ✓ | ✓ | | ✓ | ✓ | YES | ✓ | | |
| 30 Plasminogen | | ✓ | ✓ | | ✓ | ✓ | YES | ✓ | Cardiovascular; Enzyme of thrombolysis | Anderson, 2005 |
| 31 Transferrin | YES | ✓ | ✓ | ✓ | ✓ | ✓ | YES | ✓ | Cardiovascular; Associated with hypercholesterolemia, iron levels | Berhane, 2005 |
| 32 Transthyretin | YES | ✓ | ✓ | ✓ | ✓ | ✓ | YES | ✓ | | |
| 33 Vitamin D binding protein | YES | ✓ | | | ✓ | ✓ | YES | ✓ | | |
| 34 Zinc alpha 2 glycoprotein | YES | ✓ | | | ✓ | ✓ | YES | ✓ | | |
| 1 Alpha-2-antiplasmin | | ✓ | | | | ✓ | ** | ✓ | Cardiovascular; Regulator, fibrinolytic system | Anderson, 2005 |
| 2 Apolipoprotein E | | ✓ | | | | ✓ | ** | ✓ | Cardiovascular; Epsilons allele marker | Anderson, 2005 |
| 3 Apolipoprotein L1 | | ✓ | | | | ✓ | ** | ✓ | Cardiovascular; Lipoprotein | Anderson, 2005 |
| 4 Beta thromoglobulin | | ✓ | | | | ✓ | ** | | | |
| 5 Carbonic anhydrase I | YES | ✓ | | | | ✓ | ** | | | |
| 6 Complement component 3 | | ✓ | | | | ✓ | ** | ✓ | Cardiovascular; Previous myocardial infraction assc. | Anderson, 2005 |
| 7 Complement factor B | | ✓ | | | | ✓ | ** | ✓ | | |

TABLE 1-continued

Proteins identified in the albumin-binding protein/peptide complex (ABPPC).

| Protein | Intact? | Whole | SEC A | SEC B | SEC C | Anti-HSA Retentate | Bound? **, ***, # | In Depleted Serum? | Biomarker Class; Justification | Reference |
|---|---|---|---|---|---|---|---|---|---|---|
| 8 Desmoplakin | | ✓ | | | | ✓ | ** | ✓ | Cardiovascular; arrhythmogenic right ventricular cardiomyopathy | Rampazzo, 2002 |
| 9 Fibrinogen, alpha chain | | ✓ | | | | ✓ | ** | | Cardiovascular; Cardiovascular risk relation | Anderson, 2005 |
| 10 Gelsolin | YES | ✓ | | | | ✓ | ** | ✓ | Signaling Protein in plasma; Ca2+ channel inactivation in heart | Berhane, 2005 |
| 11 Histidine rich glycoprotein | | ✓ | | | | ✓ | ** | ✓ | Cardiovascular; Assoc. w/blood coagulation and fibrinolysis | Shigekiyo, 1996 |
| 12 Lumican | YES | ✓ | | | | ✓ | ** | ✓ | Cardiovascular; Assoc. w/ coronary atherosclerosis | Berhane, 2005 |
| 13 Prothrombin | | ✓ | | | | ✓ | ** | | Cardiovascular; Coagulation | Anderson, 2005 |
| 14 Serum Amyloid A4 | | ✓ | | | | ✓ | ** | | Cardiovascular; Marker, acute myocardial infraction | Berhane, 2005 |
| 15 Vitronectin | | ✓ | | | | ✓ | ** | ✓ | Cardiovascular; Cofactor, inhibition of activated protein C | Anderson, 2005 |
| 1 Actin, beta | | | ✓ | ✓ | | | *** | ✓ | | |
| 2 Attractin | | | ✓ | ✓ | | | *** | | | |
| 3 Inter alpha trypsin heavy inhibitor chain H2 | | | ✓ | ✓ | | | *** | ✓ | | |
| 4 Macroglobulin, alpha 2 | | | ✓ | ✓ | | | *** | ✓ | Cardiovascular; inhibitor, plasma protease | Anderson, 2005 |
| 5 Monocyte differentiation antigen CD14 | | | ✓ | ✓ | | | *** | | Cardiovascular; Mediates inflammatory response | Berhane, 2005 |
| 6 Pregnancy zone protein | | | ✓ | ✓ | | | *** | | | |
| 7 Retinol binding protein | YES | | ✓ | ✓ | | | # | ✓ | Inflammation; Assoc. with inflammatory response | Rosaies, 1996 |

** Proteins found in the Anti-HSA retentate (indicating bound to albumin) but absent in SEC; therefore not confirmed as bound to albumin
*** Proteins found in the high MW SEC fraction but not in the anti-HAS retentate and are not confirmed as bound to albumin.
Retinol binding protein was found in the high MW SEC fraction but not found in the anti-HSA retentate. However, it is a reported albumin-binding protein.

Eluting near 116 kDa, SEC-A appeared similar in MW to a band visualized on 1D SDS-PAGE at 116 kDa. As expected, this fraction contains proteins with MW>100 kDa (n=6). Additionally, this fraction also contains 26 proteins with MWs well below 100 kDa, indicating that they must be associated with some other protein/s in order to be eluting at the higher molecular weight under native conditions. As can be clearly seen by gel (FIG. 5) several bands in SEC-A are only present after heating 10 min at 90° C., including retinol binding protein, clusterin, and paraoxonase 1. SEC-B, containing fractions eluting near 100 kDa, is expected to be a mixture of proteins found in SEC-A and SEC-C since the tail ends of these peaks overlapped in SEC-B, and the overlapping bands are clear in FIG. 5. SEC-C contains fractions eluting near 66 kDa. As with SEC-A, many bands are present only after heating of this sample and the fraction includes many proteins with MWs well below 66 kDa, including alpha-1-acid glycoprotein 1, alpha-2HS-glycoprotein, and zinc alpha 2 glycoprotein. In summary, the SEC results show a number of proteins eluting at MWs much higher than their expected MWs under native conditions, suggesting that they are associated with another proteins, potentially albumin, to form higher molecular weight complexes. Albumin was observed in each of the SEC fractions, suggesting that it is possible that albumin is present in a variety of complexes, containing different proteins. In other words, albumin complexes may be heterogeneous. Thus, the SEC results support the conclusion that there are albumin-protein/peptide complexes present under native conditions.

Figure 7:
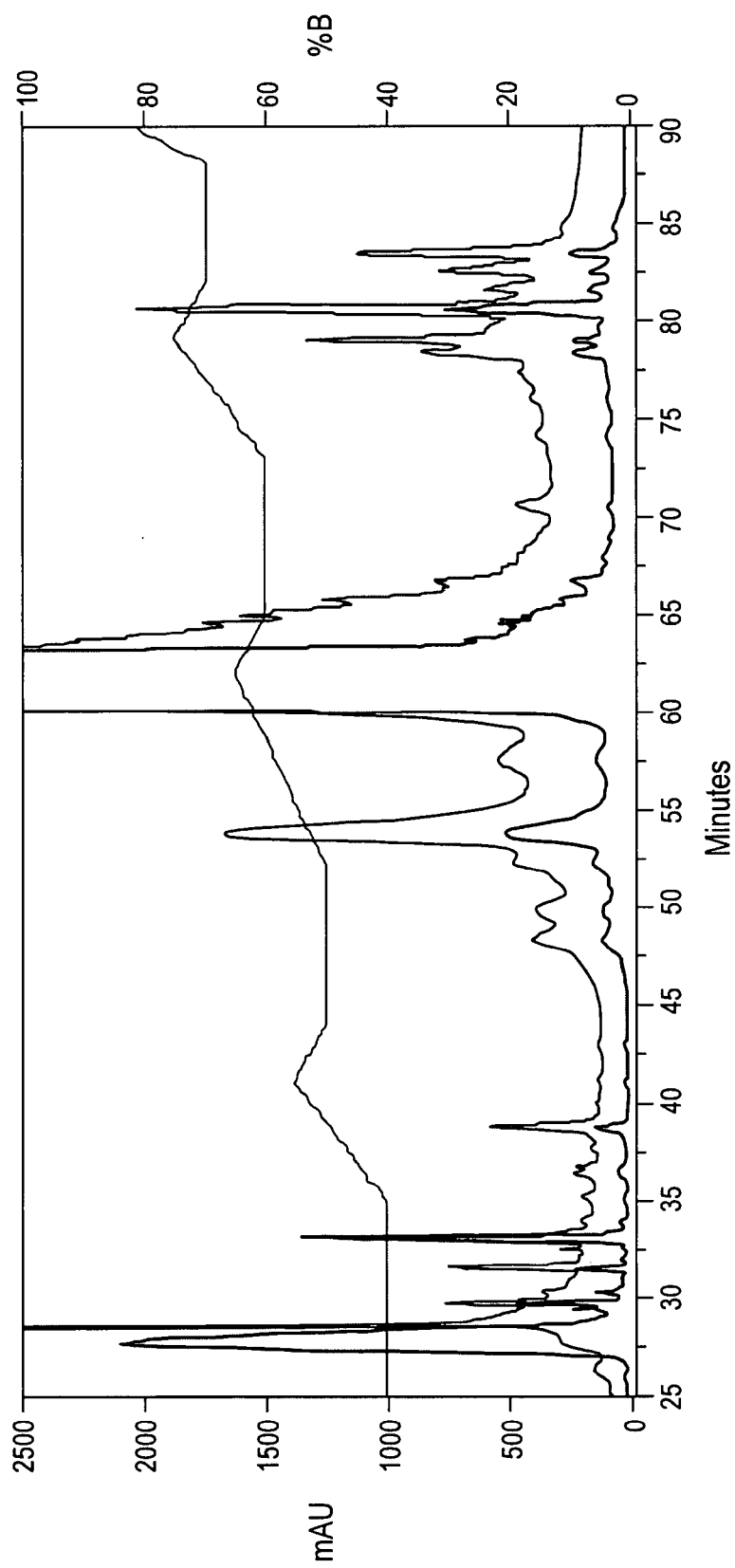
FIG. 7. RP-HPLC chromatograms of the anti-HSA retentate of the albumin-enriched fraction from normal pooled serum.

The anti-HSA immunoaffinity column was used to confirm the SEC results and to further probe specifically for interactions of proteins with albumin. The anti-HSA kit is designed to specifically remove >95% of albumin from human serum with no cross-reactivity to other serum proteins. Therefore, it was predicted that by passing the albumin-enriched fraction over the anti-HSA column, those proteins and peptides not bound to albumin would flow through and those bound to albumin would remain bound to albumin as it binds to the column. The proteins and peptides bound to the anti-HSA column (i.e. retentate) were analyzed directly by MALDI-TOF MS, 1D SDS-PAGE (FIG. 5), and further separated by RP-HPLC (FIG. 7) prior to MALDI-TOF MS/MS and LC-MS/MS. Each of these techniques revealed a number of other proteins in addition to albumin present in the retentate (Table 1). 34 of the 49 proteins identified in the anti-HSA retentate were also observed in the SEC fractions A-C, confirming that they are indeed associated with albumin, either directly or indirectly.

Fifteen proteins were found in the anti-HSA retentate but not in any of the SEC fractions and could not be confirmed as bound, but are noted in Table 1 as potentially bound. Similarly, seven proteins were found in the SEC-A, but not in the anti-HSA, and therefore could not be confirmed as being bound to albumin. However, four (attractin, alpha 2 macroglobulin, pregnancy zone protein, and complement component 4A) of these seven proteins in the SEC fractions have molecular weights above 100 kDa, and are therefore expected to elute in SEC-A even if not associated with other proteins. Actin and monocyte differentiation antigen CD 14" have molecular weights below 100 kDa, but are known to associate with other proteins found in the albumin-enriched fraction, and therefore these proteins could be forming complexes, resulting in their elution at a higher molecular weight. Only one protein, retinol binding protein, was found in SEC-A and was expected to be found in the anti-HSA retentate due to its known binding to albumin, yet was not observed in the anti-HSA retentate. In summary, 34 proteins were confirmed as bound to albumin and 16 additional proteins are potentially bound. The least abundant albumin binding proteins range 1.0E+1-1.0E+3 pg/ml in normal serum (carbonic anyhdrase I, fibrinogen alph chain, beta thromboglobulin). Consequently, the dynamic range of proteins bound (i.e. not just high abundance proteins), the fact that the albumin-protein/peptide complexes exhibit tight binding (i.e. complexes observed in presence of SDS and are therefore not non-specific), and the fact that whole proteins, not just peptides, are binding, collectively indicate that albumin is binding proteins specifically. Finally, by combining the MW observed by MALDI-TOF MS, location on 1D SDS-PAGE, and sequence coverage observed, we are able to confirm that the intact, or nearly-intact version (not merely peptides) is present for 27 of the 50 bound and potentially bound proteins, and range in MW from 8.7 to 119 kDa.

The list of proteins identified here was compared to the comprehensive lists of cardiovascular biomarkers compiled by Anderson, et al (14) and Berhane, et al (15). Additionally, a literature search for other types of biomarkers was also conducted (14-20). A summary of the results from these searches is provided in Table 1. Interestingly, 39 proteins in the ABPPC have been previously reported to be potential biomarkers, with most of these related to cardiovascular diseases. Perhaps the most interesting potential biomarkers in the ABPPC are those proteins that were not observed in the albumin-depleted fraction. Proteins in this category are alpha-2HS-glycoprotein, apolipoprotein A1, ceruloplasmin, inter-alpha trypsin inhibitor H4, kininogen, apolipoprotein CIII, carboxypeptides B2, fibrinogen, prothrombin, serum amyloid A4, and beta thromboglobulin. Interestingly, all of these proteins, except beta thromboglobulin, are reported to be potential cardiovascular biomarkers. Beta thromboglobulin is a chemokine that is normally present at low levels in serum and is involved in immune response. Of further interest is that alpha-2HS-glycoprotein, apolipoprotein A1, apolipoprotein CIII, and ceruloplasmin were observed in intact form.

Example 4

Identification of ABPPC Biomarkers in Myocardial Infarction

Figure 8:
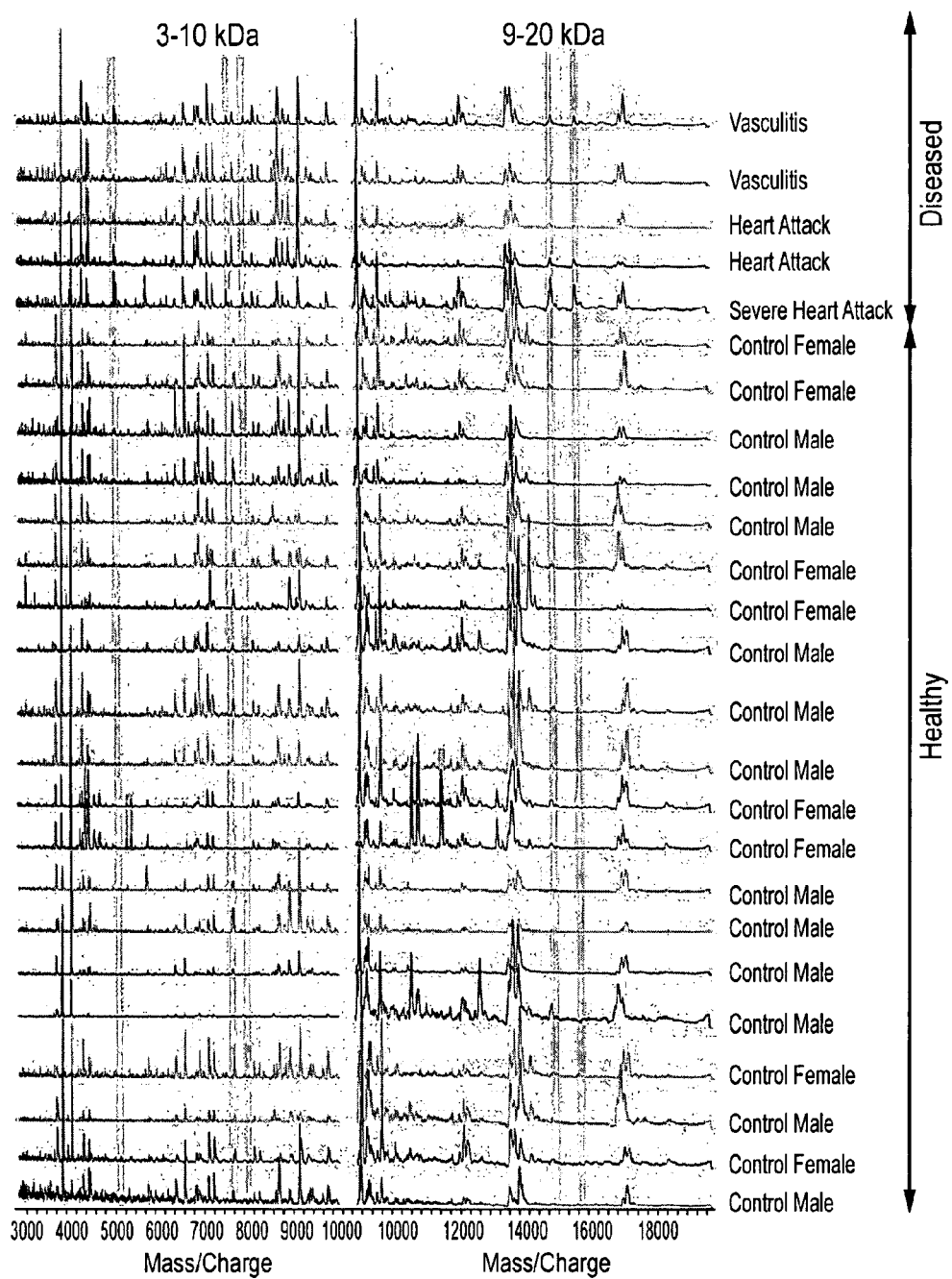
FIG. 8. MALDI-TOF spectra of 20 healthy controls and 5 diseased patients. Differences are highlighted in yellow.

The albumin-enriched fraction of healthy and diseased individuals were compared by several methods in order to determine if any changes, representative of or correlating to disease, could be detected. Comparison of the MALDI-TOF spectra of the whole albumin enriched fraction of 20 healthy controls to 5 diseased patients (2 vasculitis, 3 acute myocardial infarction (AMI) revealed 5 interesting differences (FIG. 8). These peaks were present only in the diseased samples, and at higher intensity in the severe AMI than the other diseased patients.

Figure 9:
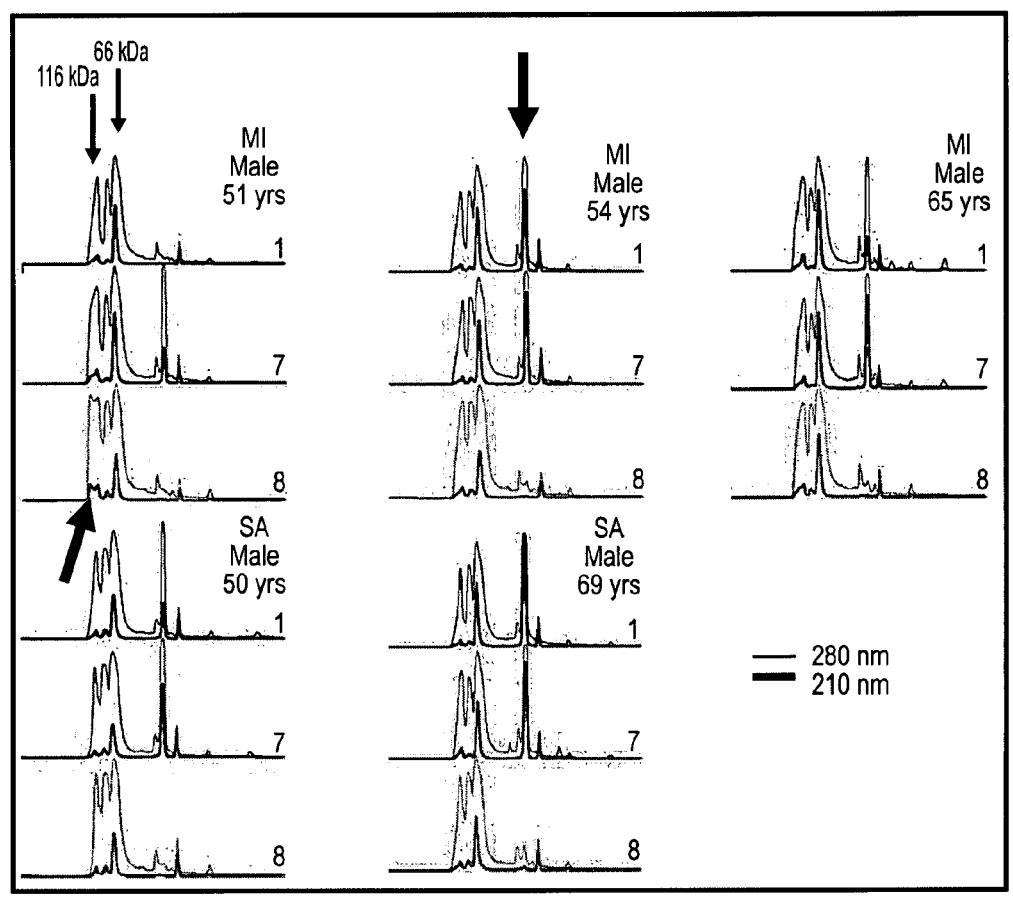
FIG. 9. SEC chromatograms of the albumin-enriched fraction of 3 timepoints from 5 patients (3 MI, 2 SA) who underwent balloon angioplasty.

In addition to whole albumin-enriched fraction, the ABPPC was compared among patients diagnosed with myocardial infarction (MI) and stable angina (SA) who came to the ER and underwent a percutaneous transluminal corollary angioplasty (PTCA) otherwise known as a balloon angioplasty. Three timepoints (#1=baseline, #7=1 hour post procedure (ischemia), and #8=24 hours post procedure (necrosis)) were analyzed by SEC followed by RP-HPLC and 1D SDS-PAGE. The SEC chromatograms of each sample (FIG. 9) show similar patterns for all samples, illustrating the reproducibility of the albumin-enriched fraction and of the SEC. However, distinct differences among times within individuals are visible. A large peak (yellow arrow) can be observed below 66 kDa in timepoints 1 and 7 for 4 of the samples, and in time point 7 only for one sample. This peak is noticeably reduced in time point 8 in all samples. Also visible in the SEC chromatogram are three peaks in the high MW region (>66 kDa). In patients with SA, the three peaks look similar among all timepoints. However, in the MI patients, the middle peak appears lower in intensity in timepoints 1 and 7 than it is in time point 8. Also, in one sample, (MI, Male 51 yrs) a $4^{th}$ peak appears at time point 8 in the high MW region (green arrow). Limited resolution of the SEC required further separation by RP-HPLC and 1D SDS-PAGE of the ABPPC in order to obtain more detail.

Figure 10A:
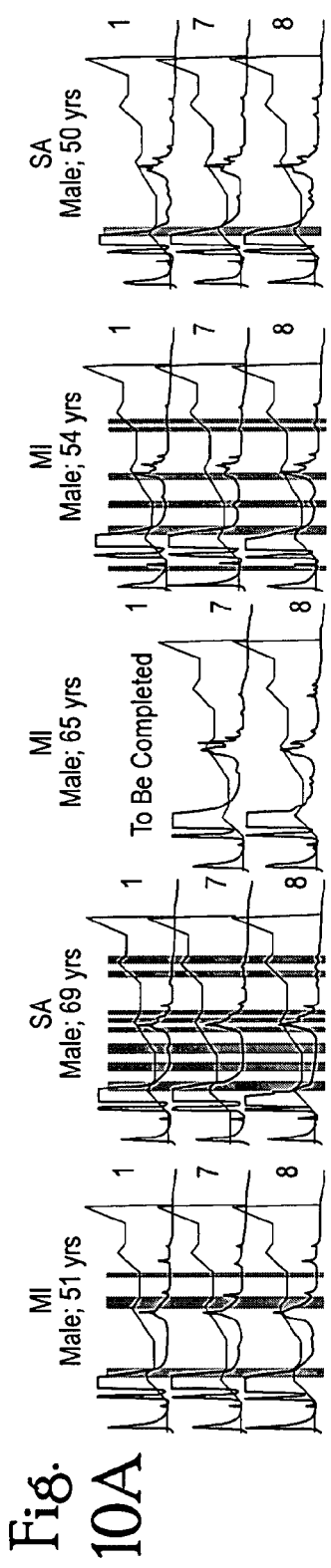
FIG. 10. Panel A shows RP-BPLC chromatograms (210 nm) of the high MW SEC fractions from FIG. 9. Yellow bars highlight differences among the 3 timepoints. Panel B shows 1D SDS-PAGE of the same fractions. Panel C shows western blot for albumin of gels in Panel B.
Figure 10B:
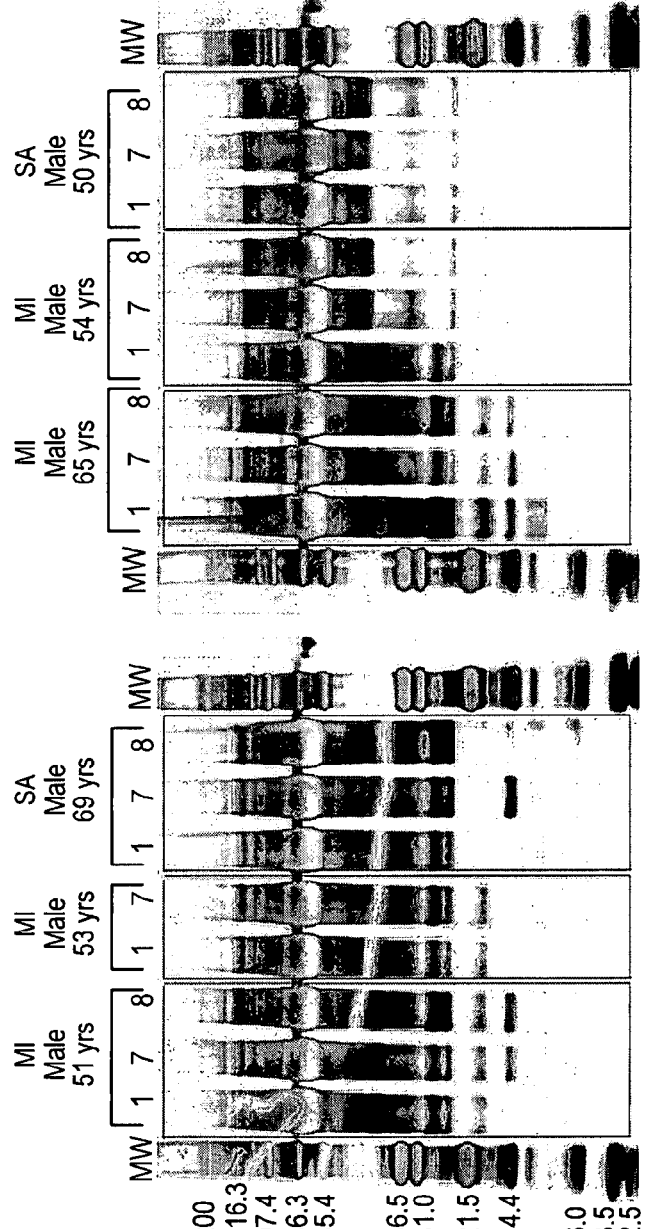
Figure 10C:
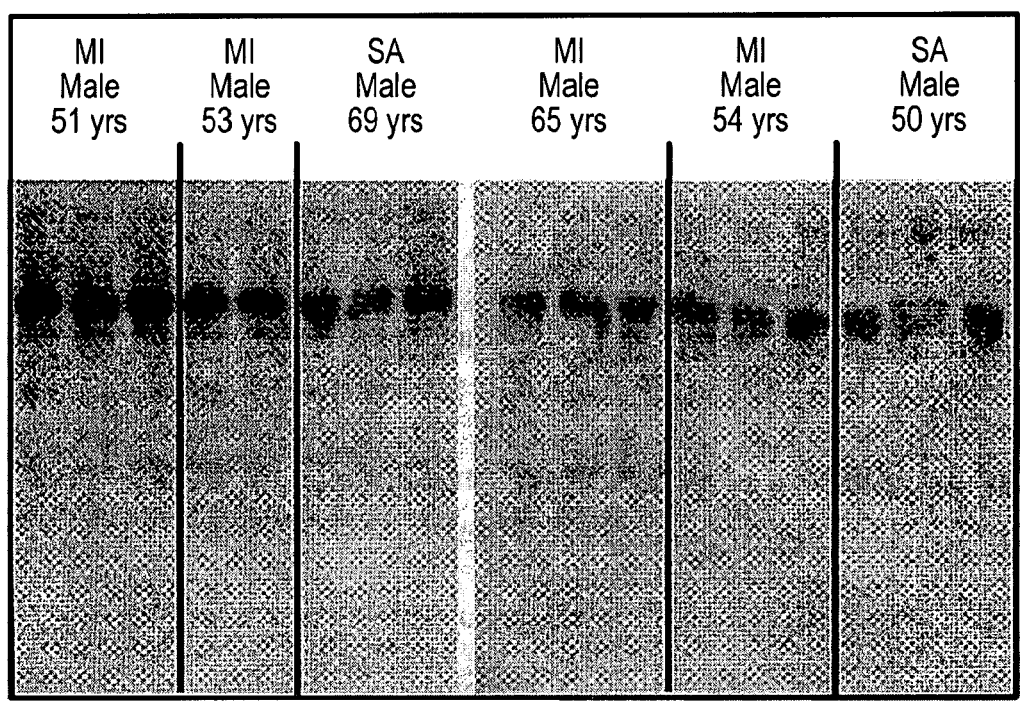
Figure 11:
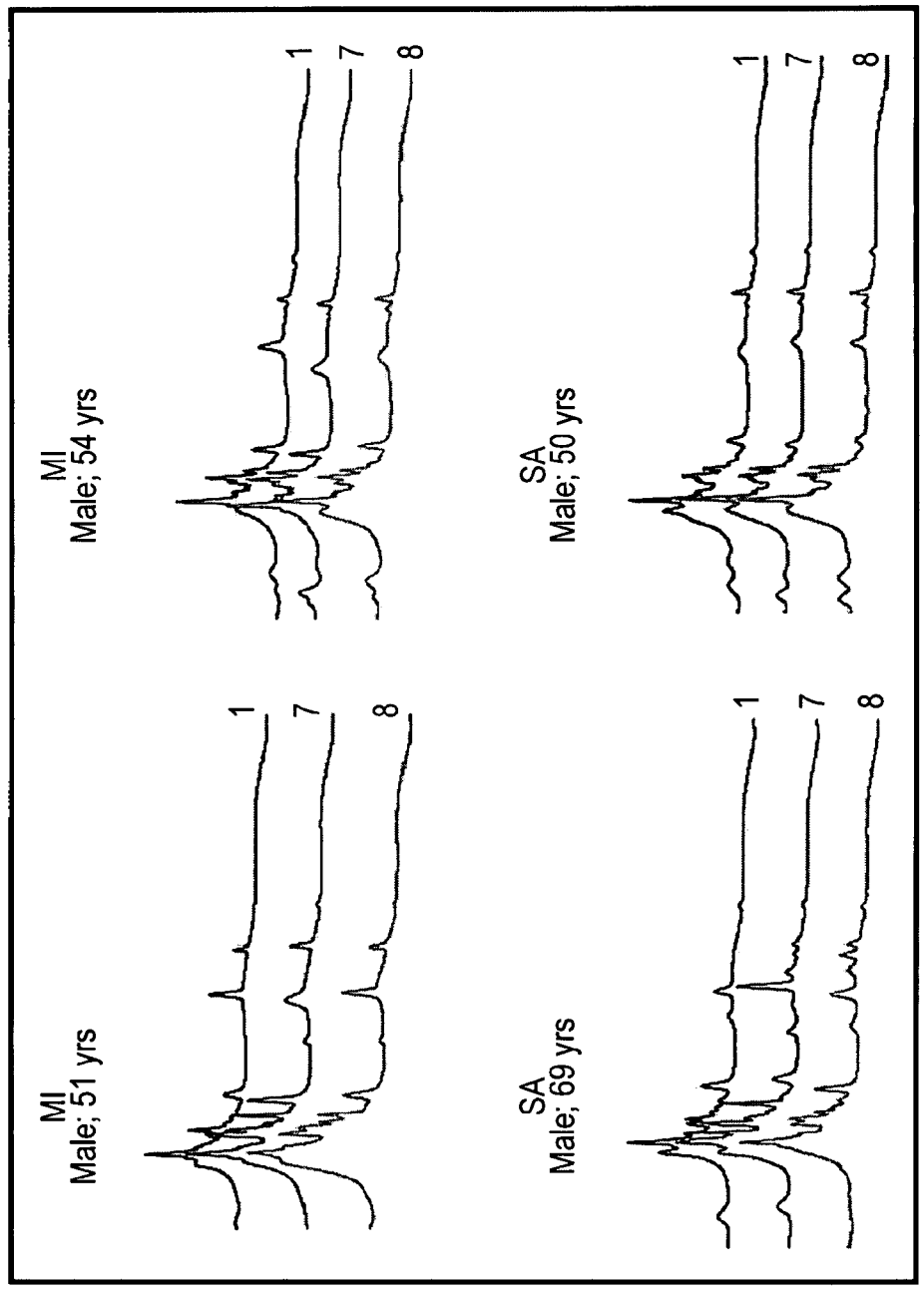
FIG. 11. Zoomed view of a section of the RP-HPLC chromatograms (in FIG. 10A) of the SEC fraction containing the ABPPC.

Upon further separation by both RP-HPLC and 1D SDS-PAGE, more detail of the ABPPC appears. Again, the RP-HPLC profiles have similar patterns among all samples, illustrating reproducibility. However, differences are apparent (highlighted in FIG. 10A and zoomed in FIG. 11). Multiple differences are present in time point 1 vs. 7&8 for all samples. It appears that fewer proteins are contained in the ABPPC in time point 1 when compared to 7 and 8. The 1D SDS-PAGE also reveals differences among timepoints within each sample as well as differences among samples. Interestingly, the MI patients contain multiple small MW bands (<31 kDa) in the high MW SEC that the SA samples lack. While protein IDs have not been obtained for these particular samples, the proteins contained in the small MW bands of gels with similar banding patterns are apolipoprotein AI, haptoglobin, retinol binding protein, and transthyretin, Also, the band slightly above 116 kDa appears darker in the MI samples (51, 65 yrs). In previous gels this band was identified as ceruloplasmin. Western blot analysis (FIG. 10C) of the gels of the high MW SEC fractions show albumin present in the band near 116 kDa in addition to multiple smaller MW bands, presumably fragment bands. Quantitative analysis of the albumin present in intact form (at 66 kDa) vs. the albumin present in low MW fragments from the western blot revealed an interesting trend. The ratio of whole albumin:albumin fragments in the MI samples on average was 1.47, while the ratio in SA samples was 4.57, with a t-test score of 0.01. Consequently, the selective and specific proteolysis of albumin, or the change in albumin that makes it more susceptible to thermal degradation, in MI vs SA should be a useful a biomarker.

Figure 12:
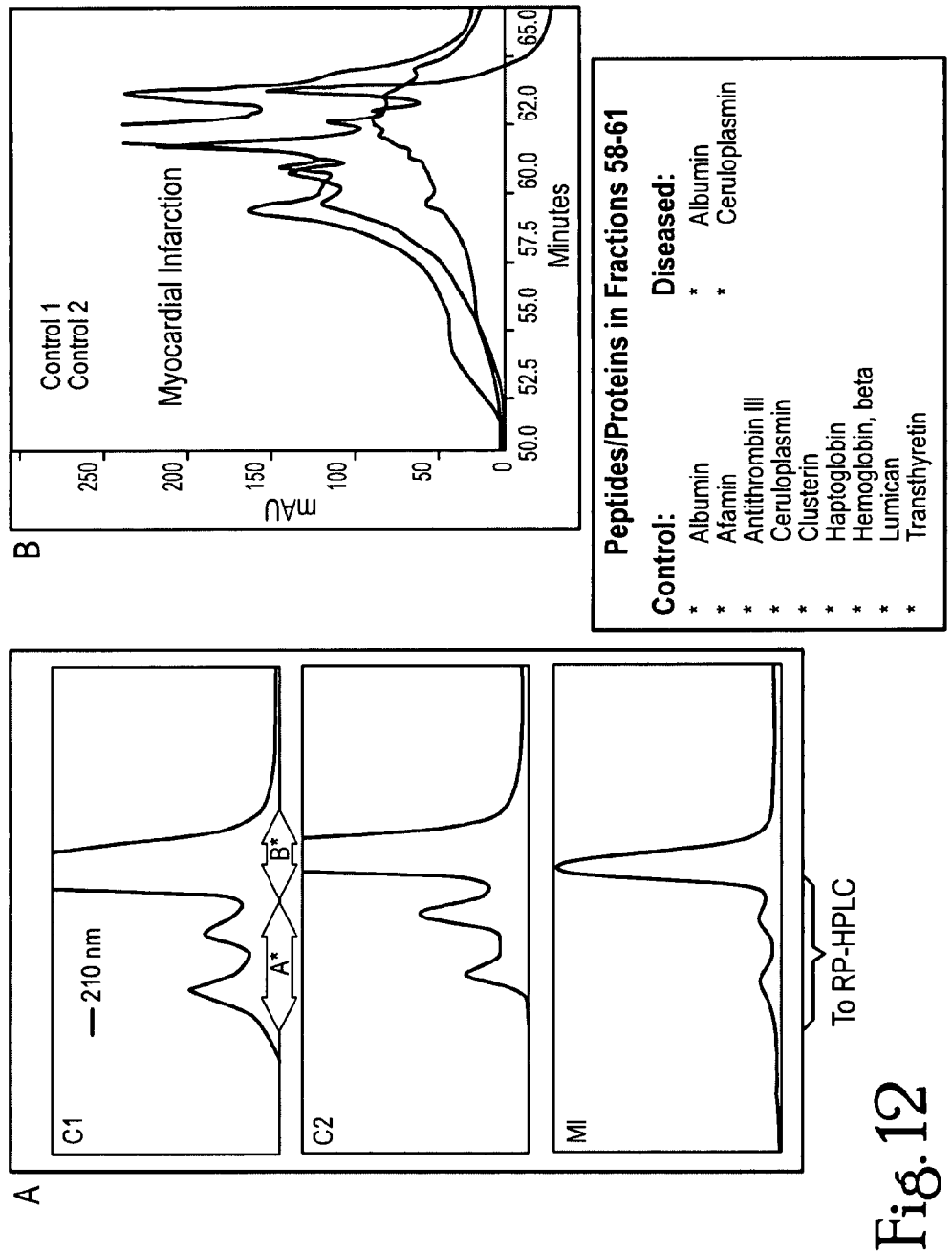
FIG. 12. SEC chromatograms (280 nm) of two healthy controls and a patient with a myocardial infarction (A). Panel B shows RP-HPLC chromatograms of the high MW SEC fractions from the samples in Panel A.

More detailed analysis was performed on a different set of samples, 2 healthy controls and a patient with MI. The ABPPC was isolated by SEC, and split into two fractions, SECA* and SECB* (FIG. 12A). Differences among diseased and control are clearly visible in the reduced peak heights of the 2 large MW peaks. SECA* was then separated by RP-HPLC (FIG. 12B). The MI sample had significantly reduced peak intensity at retention times 50-64 min. Further analysis by LC-MS/MS following tryptic digest of fractions 58-61 minutes revealed 7 proteins present in the healthy controls that are not present in the MI sample. This would indicate that the ABPPC contains fewer proteins in disease than in healthy.

It is noted that this set of samples was normalized by total volume, not protein concentration, prior to analysis by SEC.

Example 5

Identification of Biomarkers in Vasculitis

Figure 13:
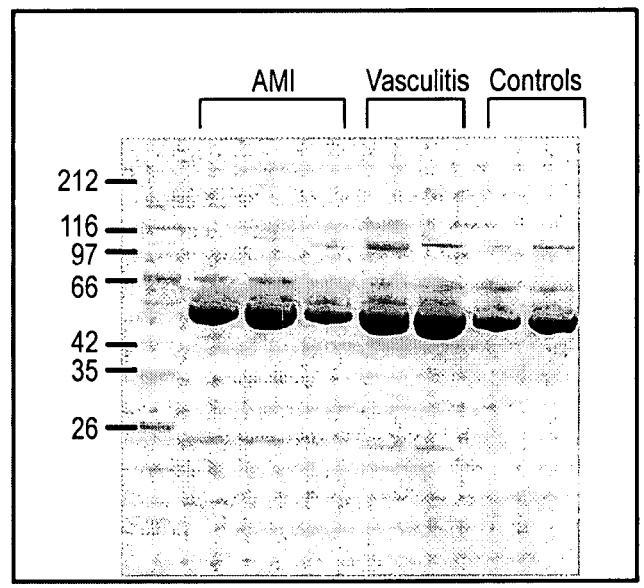
FIG. 13. 1D SDS-PAGE of the albumin-enriched fraction of 2 of healthy controls, 2 patients with AMI and 2 patients with vasculitis.

In addition to patients with MI, the albumin-enriched fraction from patients with vasculitis was also examined. The comparison of the albumin-enriched fraction from patients with AMI and vasculitis by 1D SDS-PAGE are interesting (FIG. 13). Multiple high MW bands appear in the diseased but are absent from the controls.

Example 6

Figure 14:
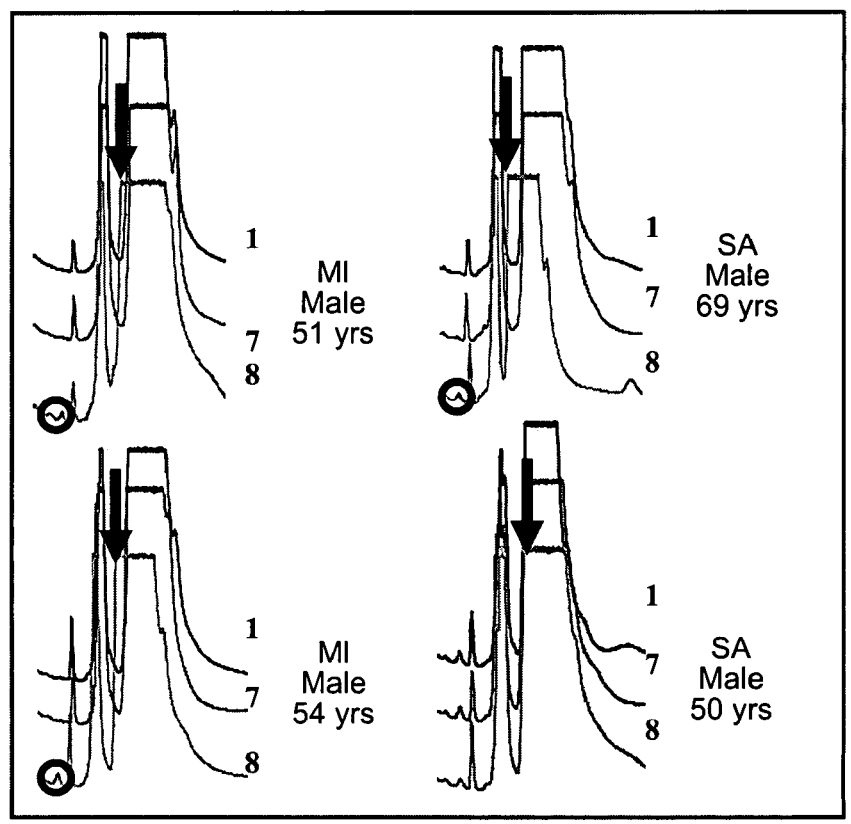
FIG. 14. RP-HPLC chromatograms of the high MW SEC fractions from FIG. 10A zoomed in to show the albumin peak. Arrows point to change in retention time for albumin in time point 8 for 2 MI and 1SA patient. Red circle highlights peak observed only in time point 8 for the same samples.

The data so far provide evidence for the existence of an ABPPC and that this complex changes in disease. This alteration of the ABPPC could be due to altered availability of particular proteins in serum in diseased vs. healthy. On the other hand, some evidence points to an alteration in the albumin itself (FIG. 14). The retention time of albumin in the RP-HPLC of the high MW SEC fractions is shifted in time point 8 in 2 patients with MI and the older patient with SA (FIG. 14, black arrow). Also interesting is the appearance of a small peak early in the chromatogram in time point 8 for the same samples (circled in red in FIG. 14).

Discussion

These observations that the ABPPC, and albumin itself, change with disease bring about important biological concerns regarding the biological role of albumin. While the cause and the nature of the change are unknown, the results presented herein provide sufficient evidence that there are changes in the ABPPC than can be detected. The opportunities for the ABPPC, in particular, to serve as a diagnostic for a variety of diseases is strengthened by the fact that it is easy to reproducibly obtain, it binds intact proteins and peptides, and binds proteins specifically. The fact that only one capture reagent is required makes an ABPPC assay Amenable to high throughput analyses. Consequently, an ABPPC assay would be affordable and efficient, as one assay can cast a wide net for potential biomarkers of multiple diseases. Furthermore, as albumin is the most abundant protein in human serum, the total volume of blood required for an ABPPC assay is small. This translates to minimal invasiveness, which is important in neonatology, pediatrics and to those patients where blood loss has been severe. Applications of the ABPPC as a diagnostic include multiple scenarios. The ABPPC can be used as a single diagnostic for a single disease, or a multiplex diagnostic for multiple diseases, since the same capture reagents can be used. This feature increases the ease with which a clinical assay may be developed. Adding to this is the availability of the ABPPC in serum which therefore aids in robustness of the commercial product. In addition to a simple yes/no diagnostic, the ABPPC could also be extended to more sophisticated analyses such as differentiating disease stage, progression, or therapeutic regiment. The specific marker of disease could be a change in albumin, altered proteolysis of albumin, change in albumin affecting its vulnerability to thermal degradation, change in proteins bound to albumin, change in stoicheometry of ABPPC, ratio of free protein to that bound in the ABPPC, ratio of intact protein vs. protein fragment in the ABPPC, or a combination of any of the above. Commercial applications could include a method for capturing the ABPPC, detecting the specific proteins/peptides of interest, detecting the modification of the protein of interest, measuring the ratio of free:bound protein, measuring the ratio of intact:peptide fragment, or measuring a stoicheometry change in the ABPPC. Detection methods could include mass spectrometry or antibody systems.

We have shown several examples hereinabove of how the ABPPC is modified during disease progression. Consequently, albumin and ABPPC modifications can be used to diagnose a disease state (one state or between two states) or a continuum of the disease process. In one example, patients were undergoing induced myocardial ischemia and myocardial infarction due to balloon inflation during angioplasty. This experimental condition mimics the pathological transition in cardiac patients presenting to the emergency department with chest pain. Myocardial ischemia (a potential form of myocardial stunning) occurs when there is reduced or no blood flow to a region of the heart. The heart compensates for this restricted flow, but ultimately if the ischemia is sufficiently severe (both in extent and/or duration) myocytes will undergo apoptosis and/or necrosis (myocardial infarction). Thus, the detection of myocardial ischemia will allow earlier diagnosis of patients that are at risk of developing AMI. These patients can then obtain earlier treatment with tissue-type plasminogen activator (TPA), angioplasty or other clot reducing and protective agents, or have their status elevated for increased care and monitoring. It is well documented that earlier reperfusion therapy saves myocardium. Therefore, early detection of vulnerable myocardium would be beneficial. Currently, there are two approaches for diagnostics for early detection i) development of a more sensitive myocardial necrosis marker for earlier detection or ii) development of an ischemic specific marker. There are only a few proposed markers of ischemia and only one that has FDA approval. This is the modified albumin (modified metal binding) which is used to rule out AMI when used in conjunction with an absent necrosis marker. In the current application, we outline the unique profile in which albumin and its binding complex (ABPPC) changes with ischemia and then further changes with AMI (cell necrosis). Thus, the ABPPC allows one to distinguish between baseline healthy individual (and those with stable angina) and encroaching ischemia and AMI. In the second case, we show changes in the ABPPC with patients already diagnosed with vasculitis. The majority of patients with vasculitis will go into remission following treatment, but most will flare and subsequently need to reestablish therapy. A valuable diagnostic for vasculitis, is therefore, one with the ability to predict when an individual will have a flare. In the comparison between vasculitis patients in remission and the subsequent flare, unique profiles of albumin and the ABPPC were obtained. Thus, the ABPPC could be used to distinguish between baseline healthy, individuals with vasculitis in remission, and those with vasculitis in flare.

REFERENCES CITED HEREIN ARE LISTED BELOW FOR CONVENIENCE (1) Millea, K.; Krull, I. *Journal of Liquid Chromatography and Related Technologies* 2003, 26, 2195-2224.
(2) Anderson, N. L.; Anderson, N. G. *Mol Cell Proteomics* 2002, 1, 845-867.
(3) Carter, D. C.; Ho, J. X. *Adv Protein Chem* 1994, 45, 153-203.
(4) Peters, T., Jr. *All About Albumin*; Academic Press: San Diego, 1996.
(5) Baczynskyj, L.; Bronson, G. E.; Kubiak, T. M. *Rapid Commun Mass Spectrom* 1994, 8, 280-286.
(6) Carter, W. A. *Methods Enzymol* 1981, 78, 576-582.
(7) Sjobring, U.; Bjorck, L.; Kastem, W. *J Biol Chem* 1991, 266, 399-405.

(8) Tirumalai, R. S.; Chan, K. C.; Prieto, D. A.; Issaq, H. J.; Conrads, T. P.; Veenstra, T. D. *Mol Cell Proteomics* 2003, 2, 1096-1103.

(9) Ortigoza-Ferado, J.; Richter, R. J.; Hornung, S. K.; Motulsky, A. G.; Furlong, C. E. *Am J Hum Genet* 1984, 36, 295-305.

(10) Krauss, E.; Polnaszek, C. F.; Scheeler, D. A.; Halsall, H. B.; Eckfeldt, J. H.; Holtzman, J. L. *J Pharmacol Exp Ther* 1986, 239, 754-759.

(11) Kelso, G. J.; Stuart, W. D.; Richter, R. J.; Furlong, C. E.; Jordan-Starck, T. C.; Harmony, J. A. *Biochemistry* 1994, 33, 832-839.

(12) Dergunov, A. D.; Vorotnikova, Y. Y. *Int J Biochem* 1994, 26, 933-942.

(13) Zhou, M.; Lucas, D. A.; Chan, K. C.; Issaq, H. J.; Petricoin, E. F., 3rd; Liotta, L. A.; Veenstra, T. D.; Conrads, T. P. *Electrophoresis* 2004, 25, 1289-1298.

(14) Anderson, L. *J Physiol* 2005, 563, 23-60.

(15) Berhane, B. T.; Zong, C.; Liem, D. A.; Huang, A.; Le, S.; Edmondson, R. D.; Jones, R. C.; Qiao, X.; Whitelegge, J. P.; Ping, P.; Vondriska, T. M. *Proteomics* 2005, 5, 3520-3530.

(16) Gonzalez-Conejero, R.; Lozano, M. L.; Rivera, J.; Corral, J.; Iniesta, J. A.; Moraleda, J. M.; Vicente, V. *Blood* 1998, 92, 2771-2776.

(17) Fujita, Y.; Ezura, Y.; Emi, M.; Sato, K.; Takada, D.; Eno, Y.; Katayama, Y.; Takahashi, K.; Kamimura, K.; Bujo, H.; Saito, Y. *J Hum Gen* 2004, 49, 24-28.

(18) Rampazzo, A.; Nava, A.; Malacrida, S.; Beffagna, G.; Bauce, B.; Rossi, V.; Zimbello, R.; Simionati, B.; Basso, C.; Thiene, G.; Tobwin, J.; Danieli, G. *Am J Hum Genet* 2002, 71, 1200-1206.

(19) Shigeldyo, T.; Yoshida, H.; Matsumoto, K.; Azuma, H.; Wakabayashi, S.; Saito, S.; Fujikawa, K.; Koide, T. *Blood* 1998, 91, 128-133.

(20) Rosales, F.; Ritter, S.; Zolfaghari, R.; Smith, J.; Ross, A. *J. Lipid Res.* 1996, 37, 962-971.

(21) Bar-or, D.; Curtis, G.; Rao, N.; Bampos, N.; Lau, E. *Eur J Biochem* 2001, 268, 42-47.

(22) Takahashi, N.; Takahashi, Y.; Putnam, F. W. *Proc Natl Acad Sci USA* 1987, 84, 7403-7407.

(23) Chan, B.; Dodsworth, N.; Woodrow, J.; Tucker, A.; Harris, R. *Eur J Biochem* 1995, 227, 524-528.

(24) Crosby, P. A. M., Deborah L In *PCT Int. Appl.: USA*, 2002.

(25) Bar-or, D. L., Edward; Winkler, James V In *PCT Int: US*, 2004.

(26) Mera, K.; Anraku, M.; Kitamura, K.; Nakajou, K.; Maruyama, T.; Tomita, K.; Otagiri, M. *Hypertens Res* 2005, 28, 973-980.

(27) Thornalley, P. J.; Argirova, M.; Ahmed, N.; Mann, V. M.; Argirov, O.; Dawnay, A. *Kidney Int* 2000, 58, 2228-2234.

(28) Murayskaya, E. V.; Lapko, A. G.; Murayskii, V. A. *Bull Exp Biol Med* 2003, 135, 433-435.

[29] Zolotarjova, N., Martosella, J., Nicol, G., Bailey, J. et al., *Proteomics* 2005, 5, 3304-3313.

[30] Fu, Q., Gamham, C. P., Elliott, S. T., Bovenkamp, D. E. et al., *Proteomics* 2005, 5, 2656-2664.

[31] Colantonio, D. A., Dunkinson, C., Bovenkamp, D. E., Van Eyk, J. E., *Proteomics* 2005, 5, 3831-3835.

[32] Chen, Y. Y., Lin, S. Y., Yeh, Y. Y., Hsiao, H. H. et al., *Electrophoresis* 2005, 26, 2117-2127.

[33] Björhall, K., Miliotis, T., Davidsson, P., *Proteomics* 2005, 5, 307-317.

[34] Chromy, B. A., Gonzales, A. D., Perkins, J., Choi, M. W. et al., *J. Proteome Res.* 2004, 3, 1120-1127.

[35] Steel, L. F., Trotter, M. G., Nakajima, P. B., Mattu, T. S. et al., *Mol. Cell. Proteomics* 2003, 2, 262-270.

[36] Stanley, B. A., Gundry, R. L., Cotter, R. J., Van Eyk, J. E., *Dis. Markers* 2004, 20, 167-178.

[37] Cohn, E. J., Strong, L. E., Hughes, W. L., Mulford, D. J. et al., *J. Am. Chem. Soc.* 1946, 68, 459-475.

We claim:

1. A method of diagnosing myocardial ischemia in a subject, comprising the steps of:
   (a) preparing an albumin enriched fraction from plasma or serum of the subject;
   (b) analyzing the albumin enriched fraction by size exclusion chromatograph (SEC) to produce SEC chromatograms of albumin-bound protein/peptide complexes (ABPPCs); and
   (c) comparing the SEC chromatograms of the ABPPCs from the subject to SEC chromatograms of ABPPCs from albumin enriched fraction from plasma or serum of a normal subject population wherein a reduction in height of at least one peak greater than or equal to about 66 kiloDaltons (kDa) in the subject is indicative of myocardial ischemia.

2. The method of claim 1, further comprising a step of analyzing the ABPPC(s) using mass spectrometry.

3. The method of claim 1, further comprising a step of analyzing the ABPPC(s) using high performance liquid chromatography, affinity chromatography, gel methods and/or immunoassay.

4. The method of claim 1 wherein the subject is a mammal.

5. The method of claim 4 wherein the subject is a human.

6. The method of claim 1 further comprising step (d) detecting the presence of an albumin-bound protein/peptide complex peak below 66 kDa.

7. The method of claim 1 further comprising the steps of:
   (d) isolating at least one ABPPC from said albumin enriched fraction from said subject wherein in said ABPPC is a protein or peptide selected from the group consisting of afamin, antithrombin III, ceruloplasmin, clusterin, haptoglobin, hemoglobin beta, lumican and transthyretin; and
   (e) comparing the ABPPC level from the albumin enriched fraction in step d) to a control level from an albumin enriched fraction from plasma or serum of a normal subject population, wherein an increase or decrease in the level of the ABPPC from the albumin enriched fraction from the subject as compared to the control level is indicative of myocardial ischemia.

* * * * *